(12) United States Patent
Harttig

(10) Patent No.: US 8,535,608 B2
(45) Date of Patent: Sep. 17, 2013

(54) ANALYTICAL SYSTEM AND METHOD FOR ITS OPERATION

(75) Inventor: Herbert Harttig, Neustadt (DE)

(73) Assignee: Roche Diagnostics Operations, Inc., Indianapolis, IN (US)

(*) Notice: Subject to any disclaimer, the term of this patent is extended or adjusted under 35 U.S.C. 154(b) by 0 days.

(21) Appl. No.: 13/104,575

(22) Filed: May 10, 2011

(65) Prior Publication Data

US 2011/0212532 A1   Sep. 1, 2011

Related U.S. Application Data

(62) Division of application No. 11/533,894, filed on Sep. 21, 2006, now abandoned.

(30) Foreign Application Priority Data

Oct. 1, 2005 (EP) .................................. 05021557

(51) Int. Cl.
*G01N 33/00* (2006.01)

(52) U.S. Cl.
USPC ........................................ 422/68.1

(58) Field of Classification Search
USPC .............................. 422/68.1, 82.05, 500, 560
See application file for complete search history.

(56) References Cited

U.S. PATENT DOCUMENTS

| | | | |
|---|---|---|---|
| 5,077,010 A | | 12/1991 | Ishizaka et al. |
| 5,489,414 A | | 2/1996 | Schreiber et al. |
| 5,989,917 A | * | 11/1999 | McAleer et al. ............ 436/46 |

FOREIGN PATENT DOCUMENTS

| | | |
|---|---|---|
| EP | 1 360 935 | 11/2003 |
| EP | 1 424 040 | 6/2004 |
| WO | WO 03/082091 A2 | 10/2003 |
| WO | WO 03/082092 A1 | 10/2003 |
| WO | WO 2005/040793 A1 | 5/2005 |
| WO | WO 2005/065828 A1 | 7/2005 |

* cited by examiner

*Primary Examiner* — Sam P Siefke
(74) *Attorney, Agent, or Firm* — Woodard, Emhardt, Moriarty, McNett & Henry LLP

(57) ABSTRACT

An analytical system comprising a replaceable magazine (12) for providing a plurality of test units that react to an analyte and a measuring device (14) for processing the test units, wherein the magazine (12) is provided with a code (26) that can be registered by the measuring device (14). In order to enable the simplest possible coding, it is proposed that the code (26) comprises an unique magazine identifier (28) for the magazine (12) and that the measuring device (14) has a magazine-independent test counter (16) which registers the processing of a test unit and a counter memory (18) to store the magazine identifier (28) and a corresponding count of the test counter (16).

11 Claims, 1 Drawing Sheet

ANALYTICAL SYSTEM AND METHOD FOR ITS OPERATION

REFERENCE TO RELATED APPLICATIONS

This application is a divisional of U.S. patent application Ser. No. 11/533,894 filed Sep. 21, 2006, which claims the benefit of European Patent Application No. 05 021 557.3 filed Oct. 1, 2005, which are both hereby incorporated by reference in their entirety.

BACKGROUND

The invention concerns an analytical system especially for carrying out patient self-monitoring such as blood sugar tests comprising a replaceable magazine for providing a plurality of test units that react to an analyte and a measuring device for (successively) processing the test units wherein the magazine is provided with a code that can be registered by the measuring device. The invention additionally concerns a method for operating such a system.

Such systems are primarily used by diabetics for blood sugar self-monitoring that is carried out several times daily as part of an insulin treatment. In order that laymen can also carry out the required steps in a simple and rapid manner, it is desirable to have a substantially automated measuring process in a compact hand-held device. This should enable a more simple handling and greater flexibility for the user which is achieved by providing test elements in magazines that can be used in measuring devices. The test is generally processed by a chemical detection reaction whose progress or end point is detected optically or electrochemically. The correlation between the measured signal that is obtained and the analyte concentration is subject to certain variations which can differ from manufacturing batch to manufacturing batch. Codes on the magazines have already been introduced in order to take into account these variations and they are used to correct the measured signal in the instrument in such a manner that the output value has a better agreement with the actual analyte concentration than the crude signal.

A hand-held analyser into which a replaceable magazine can be inserted is known from WO2005/065828. The said magazine in the form of a drum magazine can have several chambers each of which can hold one test strip distributed in the circumferential direction wherein the front ends of the magazine can be closed with sealing foil and the sealing foil is pierced when a strip is removed. Especially after a temporary removal of a drum magazine an ineffective actuation of the removal device can be prevented by means of the fact that a check device generates a signal when the chamber located in the removal position is not closed by a sealing foil.

SUMMARY

On this basis the object of the invention is to further improve the systems known in the prior art and to ensure more user friendliness and process reliability using simple means.

The combination of features stated in the independent patent claims is proposed to achieve this object. Advantageous embodiments and further developments of the invention are derived from the dependent claims.

The invention is based on the idea of enabling the consumption of test units to be detected by the instrument. Accordingly it is proposed according to the invention that the code comprises an unique magazine identifier for the magazine and that the measuring device has a magazine-independent test counter which registers the processing of a test unit and a counter memory to store the magazine identifier and a corresponding count of the test counter. As a result it is not necessary to rewrite the information about consumption on the magazine and hence it can be further simplified as a replaceable article. Dispensing with the rewriting also allows a more favourable design of the code reading device. Since the required components are anyhow present in the instrument electronics for test processing for example in the form of programmable microprocessors, an additional complicated implementation on this side is thus unnecessary.

The test counter advantageously contains an arithmetic unit for example in the form of a programme routine on a microprocessor which updates the count stored for the registered magazine identifier of a magazine according to the consumption of test units where the count gives the number of test units of a respective magazine that are used or are still available.

In order to increase the convenience it is advantageous when the count for the magazine in use can be displayed for the user on a display.

For the optional use of several magazines, it is advantageous when the counter memory has a plurality of storage locations for the storage of a plurality of magazine identifiers and associated counts. In this connection it is proposed that the test counter has a comparator to compare the magazine identifier that is read in with the magazine identifiers that are present in the counter memory. The invention provides that, on the basis of this comparison, the test counter allocates an initial count to a magazine identifier of a newly inserted magazine that has not yet been stored, and that when the magazine identifier of a newly inserted magazine agrees with a stored magazine identifier, the test counter reads out the corresponding count in the counter memory and continues to count.

The measuring device advantageously comprises an optical, magnetic, electric or electromagnetic code reader to register at least the magazine identifier. In this connection the code can be attached to the magazine as a bar-code in particular a 2-D bar-code, magnetic strip, electronic memory component, in particular an EPROM or transponder. In order to register the consumption status, the code should also include the total count of test units of a magazine.

It is particularly advantageously used in a hand-held device to exchange a magazine as a consumable unit.

The test units stored in the magazine are preferably in the form of a test tape or test strip to which body fluid can be applied.

With regard to the process the object stated above is achieved in that an unambiguous magazine identifier of the magazine is registered, the magazine identifier is allocated a count in a counter memory for the number of used or available test units and when a test unit has been processed, the counter reading is advanced without intervention on the side of the magazine.

The invention is further elucidated in the following on the basis of an embodiment example that is shown schematically in the drawing.

DESCRIPTION OF SELECTED EMBODIMENTS

Figure 1:
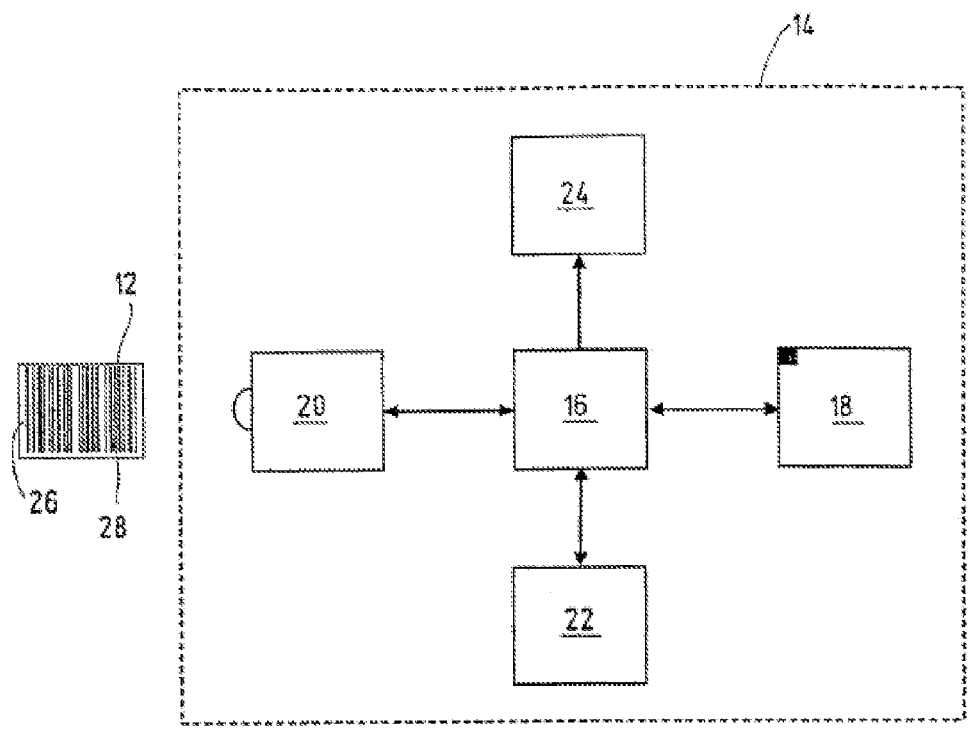
FIG. 1 shows a block diagram of an analytical system for blood sugar tests with a test counter and FIG. 2 shows the system as a hand-held device in a perspective view.

The blood sugar test system shown in FIG. 1 enables patient self-monitoring by means of a hand-held device 10 and a magazine 12 that can be used therein to provide a plurality of test units that react to an analyte (blood glucose). The test units can for example be formed by test strips in a strip magazine or by tape sections in a tape magazine (cassette) and can be successively processed in an instrument measuring device 14 to give the user a momentary picture of his blood sugar level in so-called spot measurements.

As illustrated in FIG. 1 the measuring device 14 comprises a test counter 16, a counter memory 18, a code reader 20, a test processor 22 and a display 24. The magazine 12 is provided with a bar-code 26 that can be scanned by the code reader 20 and the said bar-code includes an unique magazine identifier 28 for the magazine 12 that is currently being used. This magazine can also be exchanged by the user as a consumable unit. In this connection it is also conceivable that an opened magazine with a remainder of unused test units is again inserted. Also in this case the user should be informed by the system in a simple manner about the number of test units that have been consumed or are still available.

Figure 2:
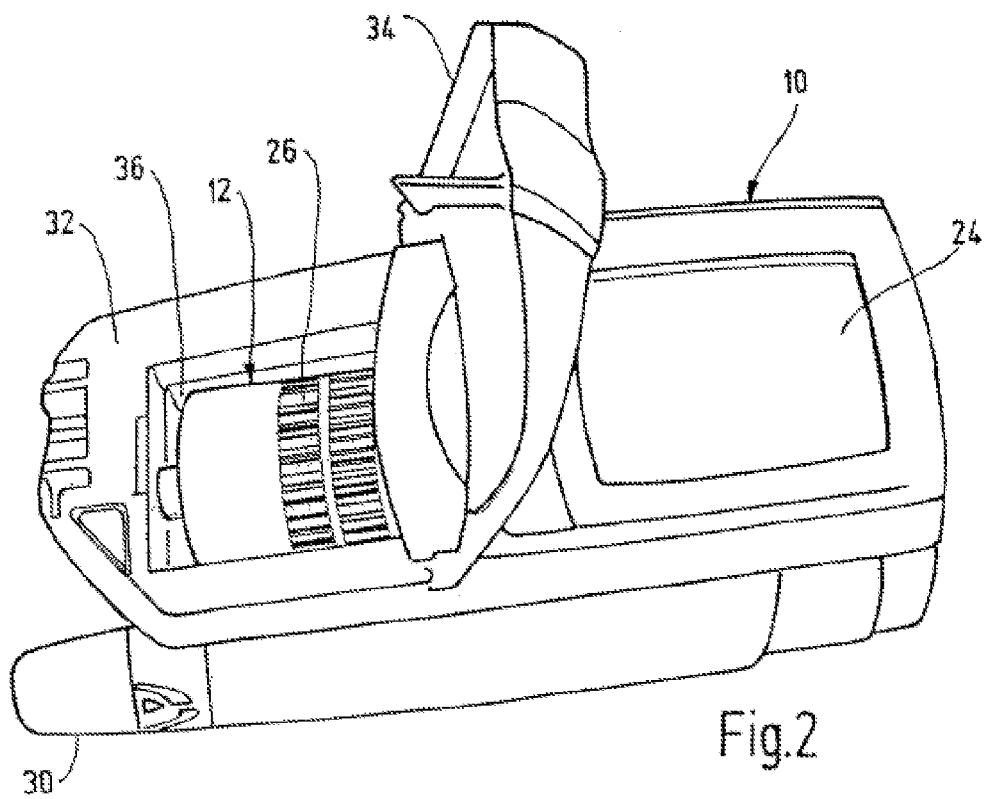

FIG. 2 shows a possible design in the form of a combined instrument which comprises a lancing aid 30 for collecting a small amount of blood from a body part and an analytical part 32 for analysing the blood sample. The analytical part 32 has a magazine slot 36 that can be closed by a lid 34 in which a drum magazine 12 containing a plurality of test strips (not shown) as test units can be inserted. A suitable drum magazine and a removal device for test strips in a hand-held analyser are known for example from WO2005/065828A1 to which reference is herewith made. The test strips can be individually pushed out of the drum magazine in order to apply blood to them wherein the analyte is detected electrochemically or photometrically in a known manner. Afterwards a new test strip can be activated for a subsequent measurement by rotating the drum magazine 26. Such a drum magazine 26 can for example contain 17 test strips whereas a considerably larger total number of test units can be realized by using a tape magazine in an appropriately designed device. A tape magazine as a cassette in a test device for body fluids is for example described in EP-A 1 424 040 to which reference is also made.

A test counter 16 which operates independently of the magazine is provided to register the consumption and which without having to rewrite and without intervention by the magazine, enables in combination with the counter memory 18 the consumption status of one or more magazines 12 to be deposited in the instrument in a simple manner. For this purpose the test counter has an arithmetic unit which is expediently realized by software which updates the counter reading that is stored for the registered magazine identifier 28 of a magazine 12 according to the consumption of test units. In this case the counter reading can give the number of used or available test units of the respective inserted magazine and is shown to the user on the display 24.

The method for determining and storing the counter reading is elucidated in more detail in the following. In addition to the magazine identifier 28, the code 26 contains further information about the total number of tests per magazine, about the production lot, production date, shelf-life and optionally about parameters to calculate the correct relationship between the measured signal and the analyte concentration in the sample. The code 26 can be written by means of a laser on a suitable label as a bar-code and attached to the magazine 12. It is also conceivable to use code carriers having a higher information density such as magnetic strips, is electronic storage components (e.g. EPROM) or transponders on the magazine 12 whereby a rewriting of the counter reading is not necessary in every case in order to allow the simplest possible instrument construction and the use of cost-effective data codes.

When a new magazine 12 is inserted, the magazine identifier 28 is read-in optically by means of a code reader 20 in a contact-free manner and compared by a comparator of the test counter 16 with the magazine identifiers that are present in the counter memory 18. In the case of a magazine identifier that has not yet been stored, an initial counter reading is allocated by the test counter whereas if there is agreement with a stored magazine identifier the corresponding counter reading in the counter memory 18 is read out. Due to a large number of storage locations, the counter memory 18 is designed to deposit a large number of magazine identifiers 28 and associated counter readings.

The test processor 22 comprises all technical instrument units for the automatic process sequence for a sample analysis. In addition to the usual analytical processing of a test unit, the processing can also include its disposal if for example the test unit has expired or the test concerned has failed. When a new test unit is processed by the test processor 22, the test counter 16 is switched further by one counter unit. The counter reading in the test counter 16 which has been correspondingly counted on is in each case written back onto the counter memory 18 together with the magazine identifier 28 so that even if the instrument is switched off or the magazine is replaced the current data combination is retained. If on the basis of the known total number of tests a counter reading of "zero" is reached when counting down, the data region of the used magazine is deleted in the counter store 18. It is, however, also possible to keep all data combinations in the counter memory. This allows all individual data allocated to magazines that have ever been used in the instrument to be read out retrospectively.

The transfer of unused magazines or cassettes between different measuring instruments is not envisaged. In such a transfer a used test unit could under certain circumstances be measured again in the second instrument provided that a reuse is physically possible. This can, however, be detected by a simple control measurement e.g. by photometric or electrical blank values without additional instrumentation and thus an erroneous measurement can be prevented. Thus a user is reliably protected from false measured values and a false treatment derived therefrom even when a blatant operating error occurs.

The invention claimed is:

1. A method for operating an analytical system, comprising:
   providing a measuring device that has a counter memory;
   loading a first replaceable magazine that has a plurality of test units into the measuring device;
   storing in a first storage location of the counter memory a first magazine identifier and associated count of test units in the first replaceable magazine;
   incrementing the count of test units associated with the first replaceable magazine in the counter memory as the test units in the first replaceable magazine are used, wherein said incrementing occurs without intervention with the magazine;
   replacing the first replaceable magazine by loading a second replaceable magazine into the measuring device;
   maintaining in the counter memory the count of the test units associated with the first replaceable magazine after said replacing;
   reading a second magazine identifier of the second replaceable magazine;

comparing the second magazine identifier with the magazine identifiers present in the counter memory of the measuring device; and storing in a second storage location of the counter memory the second magazine identifier and associated count of test units in the second replaceable magazine.

2. The method of claim 1, further comprising:

reducing the count of test units associated with the second replaceable magazine by one counter unit in the counter memory as the test units in the second replaceable magazine are used.

3. The method of claim 1, further comprising:

loading the first replaceable magazine into the measuring device;

reading the first magazine identifier of the first replaceable magazine;

determining the first magazine identifier agrees with the first magazine identifier present in the counter memory; and displaying the corresponding count of test units for the first replaceable magazine stored in the counter memory.

4. The method of claim 1, wherein said incrementing includes:

reducing the count of test units associated with the first replaceable magazine by one counter unit in the counter memory as the test units in the first replaceable magazine are used.

5. The method of claim 1, further comprising:

processing one of the test units of the first replaceable magazine with a processor to analyze a sample; and wherein said incrementing occurs in response to said processing.

6. The method of claim 5, further comprising:

determining with the measuring device that the second replaceable magazine is new based on said comparing; and wherein said storing in the second storage location of the counter memory the second magazine identifier and associated count of test units in the second replaceable magazine occurs in response to said determining.

7. The method of claim 6, further comprising:

wherein the first replaceable magazine includes a drum; and rotating the drum after said processing.

8. The method of claim 1, further comprising:

wherein the first replaceable magazine includes a tape magazine; and wherein the test units are formed by tape sections in the tape magazine.

9. A method for operating an analytical system, comprising:

providing a measuring device that has a counter memory, wherein the measuring device includes a hand-held blood glucose meter;

loading a first replaceable magazine that has a plurality of test strips into the measuring device;

storing in a first storage location of the counter memory a first magazine identifier and associated count of test strips in the first replaceable magazine;

replacing the first replaceable magazine by loading a second replaceable magazine into the measuring device;

reading a second magazine identifier of the second replaceable magazine, wherein said reading includes reading a barcode on the second replaceable magazine with a barcode reader, wherein the barcode includes a total count of test strips in the second replaceable magazine;

comparing the second magazine identifier with the magazine identifiers present in the counter memory of the measuring device;

determining with the measuring device that the second replaceable magazine is new based on said comparing;

allocating an initial counter reading of the test strips for the second magazine identifier based on the total count of the test strips from the barcode on the second replaceable magazine;

storing in a second storage location of the counter memory the second magazine identifier and the initial counter reading of the test strips in the second replaceable magazine in response to said determining;

reloading the first replaceable magazine into the measuring device after said storing;

identifying the first replaceable magazine by reading the first magazine identifier of the replaceable magazine with the hand-held blood glucose meter;

retrieving the associated count of test strips in the first replaceable magazine from the first storage location of the counter memory; and displaying the associated count of test strips in the first replaceable magazine on a display of the hand-held blood glucose meter.

10. A method for operating an analytical system, comprising:

providing a measuring device that has a counter memory;

loading a first replaceable magazine that has a plurality of test strips into the measuring device;

storing in a first storage location of the counter memory a first magazine identifier and associated count of test strips in the first replaceable magazine;

processing one of the test strips of the first replaceable magazine by analyzing a sample with the test strip;

incrementing the count of test strips associated with the first magazine identifier by one unit in the counter memory in response to said processing;

replacing the first replaceable magazine by loading a second replaceable magazine into the measuring device;

reading a second magazine identifier of the second replaceable magazine;

comparing the second magazine identifier with the magazine identifiers present in the counter memory of the measuring device;

determining with the measuring device that the second replaceable magazine is new based on said comparing;

storing in a second storage location of the counter memory the second magazine identifier and associated count of test strips in the second replaceable magazine in response to said determining;

maintaining the count of the test strips associated with the first magazine identifier in the first storage location of the counter memory after said replacing the first replaceable magazine;

unloading the second replaceable magazine from the measuring device;

reloading the first replaceable magazine into the measuring device;

reading the first magazine identifier of the first replaceable magazine;

comparing the first magazine identifier with the magazine identifiers present in the counter memory of the measuring device; and retrieving the count of test strips associated with the first magazine identifier from the first storage location of the counter memory.

11. The method of claim 10, further comprising:
wherein the first replaceable magazine includes a first replaceable drum; and
rotating the first replaceable drum after said processing.

* * * * *